United States Patent
Stark

(10) Patent No.: US 8,785,862 B2
(45) Date of Patent: Jul. 22, 2014

(54) X-RAY DETECTOR AND MEDICAL X-RAY DEVICE

(75) Inventor: Michael Stark, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 42 days.

(21) Appl. No.: 13/408,560

(22) Filed: Feb. 29, 2012

(65) Prior Publication Data

US 2012/0223238 A1    Sep. 6, 2012

(30) Foreign Application Priority Data

Mar. 2, 2011  (DE) .................... 10 2011 004 936

(51) Int. Cl.
*G01T 1/20*     (2006.01)
*G01T 1/164*    (2006.01)
*G01T 1/24*     (2006.01)

(52) U.S. Cl.
CPC .............. G01T 1/1642 (2013.01); G01T 1/24 (2013.01); G01T 1/2018 (2013.01)
USPC ............. 250/363.01; 250/366; 250/370.09; 250/370.11; 250/370.14

(58) Field of Classification Search
CPC .......... G01T 1/2018; G01T 1/24; G01T 1/642
USPC ............ 250/363.01, 366, 370.09, 370.11, 250/370.14
See application file for complete search history.

(56) References Cited

U.S. PATENT DOCUMENTS

| | | | |
|---|---|---|---|
| 4,870,667 A * | 9/1989 | Brunnett et al. ............... 378/19 |
| 5,354,695 A | 10/1994 | Leedy ............................. 437/7 |
| 6,452,186 B1 * | 9/2002 | Wieczorek et al. ...... 250/370.11 |
| 6,744,052 B1 * | 6/2004 | Petersson et al. ........ 250/370.11 |
| 6,969,899 B2 * | 11/2005 | Yaung et al. .................. 257/436 |
| 7,010,086 B2 * | 3/2006 | Chopra ............................ 378/22 |
| 7,151,287 B1 * | 12/2006 | Scheffer et al. ............... 257/292 |
| 7,161,155 B1 * | 1/2007 | Deych ....................... 250/370.11 |
| 7,974,805 B2 * | 7/2011 | Scheffer ........................ 702/104 |
| 2005/0040445 A1 * | 2/2005 | Mouli ........................... 257/290 |
| 2005/0051841 A1 * | 3/2005 | Leedy ............................ 257/347 |
| 2005/0157841 A1 * | 7/2005 | Chopra ............................ 378/22 |
| 2006/0214226 A1 * | 9/2006 | Chen et al. .................... 257/347 |
| 2006/0289777 A1 * | 12/2006 | Li et al. .................... 250/370.14 |
| 2008/0191260 A1 * | 8/2008 | De Vreede et al. ........... 257/312 |

FOREIGN PATENT DOCUMENTS

| | | | | |
|---|---|---|---|---|
| DE | 19743523 A1 | 4/1999 | ............... H05G 1/64 |
| DE | 19944731 A1 | 4/2001 | ............ H01L 27/146 |

OTHER PUBLICATIONS

German Office Action, German Patent Application No. 10 2011 004 936.3, 5 pages, Nov. 9, 2011.

* cited by examiner

*Primary Examiner* — David Porta
*Assistant Examiner* — Djura Malevic
(74) *Attorney, Agent, or Firm* — King & Spalding L.L.P.

(57) ABSTRACT

An X-ray detector having an active array comprising pixel elements for detecting X-ray radiation is provided to enable high-quality X-ray imaging, wherein each pixel element has a scintillator layer for converting X-ray radiation into light and a photodiode produced by means of CMOS technology for converting light into a measurable electrical signal, and wherein the pixel elements are arranged on a silicon substrate and a BOX (buried oxide) layer is sandwiched between the silicon substrate and the photodiode.

14 Claims, 1 Drawing Sheet

X-RAY DETECTOR AND MEDICAL X-RAY DEVICE

CROSS-REFERENCE TO RELATED APPLICATIONS

This application claims priority to DE Patent Application No. 10 2011 004 936.3 filed Mar. 2, 2011. The contents of which is incorporated herein by reference in its entirety.

TECHNICAL FIELD

This disclosure relates to an X-ray detector and a medical X-ray device.

BACKGROUND

X-ray detectors for measuring X-ray radiation are typically implemented on the basis of the principle that the X-ray radiation is absorbed and a measurable signal is generated therefrom. The X-rays can be absorbed either by means of scintillators or by means of direct converters. In X-ray detectors comprising scintillators the X-ray quanta are converted into light by means of the scintillator and the light is measured by an array of photodiodes and converted into a measurable electrical signal. Photodiodes can be produced either on the basis of amorphous silicon which is arranged on a glass substrate or as what are referred to as active pixel sensors (APSs) on the basis of CMOS technology. CMOS photodiodes have certain advantages compared with other photodiodes (e.g. pixel sensors based on amorphous silicon); they consume less power, for example, and can be manufactured with a much smaller footprint and at considerably lower cost, as well as with additional integrated readout logic. However, they also have one disadvantage: X-ray radiation that has not been absorbed in the scintillator can be absorbed in the silicon substrate arranged underneath the CMOS photodiode and generate charges there which then diffuse into the photodiode and produce a strong noise signal there (referred to as a direct hit). Noise signals of this type are visible as a bright spot on an X-ray image and degrade the quality of the X-ray image, in particular in image sequences having a low X-ray dose (fluoro scene).

SUMMARY

In one embodiment, an X-ray detector includes an active array comprising pixel elements for detecting X-ray radiation, wherein each pixel element has a scintillator layer for converting X-ray radiation into light and a photodiode produced by means of CMOS technology for converting light into a measurable electrical signal, and wherein the pixel elements are arranged on a silicon substrate and a buried oxide layer is sandwiched between the silicon substrate and the photodiode.

In a further embodiment, the photodiode is embedded in an epitaxial silicon layer. In a further embodiment, the thickness of the epitaxial silicon layer is embodied so as to be aligned to the wavelength of the light that can be generated in the scintillator layer. In a further embodiment, the thickness of the epitaxial silicon layer is embodied in such a way that between 90% and 98%, in particular 95%, of the light generated by the scintillator layer can be absorbed. In a further embodiment, the buried oxide layer has a thickness of between 40 nm and 100 nm. In a further embodiment, the active array is embodied as an active pixel sensor.

In another embodiment, a medical X-ray device includes an X-ray source and an X-ray detector, the X-ray detector including an active array comprising pixel elements for detecting X-ray radiation, wherein each pixel element has a scintillator layer for converting X-ray radiation into light and a photodiode produced by means of CMOS technology for converting light into a measurable electrical signal, and wherein the pixel elements are arranged on a silicon substrate and a buried oxide layer is sandwiched between the silicon substrate and the photodiode.

BRIEF DESCRIPTION OF THE DRAWINGS

Example embodiments will be explained in more detail below with reference to figures, in which.

DETAILED DESCRIPTION

Some embodiments provide an X-ray detector that provides advantages of CMOS technology and at the same time reduces noise signals generated due to direct hits.

Thus, some embodiments provide an X-ray detector having an active array comprising pixel elements for detecting X-ray radiation, each pixel element having a scintillator layer for converting X-ray radiation into light and a photodiode produced by means of CMOS technology for converting light into a measurable electrical signal, wherein the pixel elements are arranged on a silicon substrate. In order to avoid direct hits, i.e., noise signals caused by X-ray quanta absorbed by the silicon substrate, a layer known as a buried oxide (BOX) layer may be sandwiched between the silicon substrate and the photodiode. This layer has the effect of stopping the undesirable charges generated in the substrate from being able to contribute to the measurable signal by preventing electrical conduction through the insulating buried oxide layer. Thus, in some embodiments the X-ray detector may provide high-quality and virtually noise-free X-ray imaging. In this way advantages that an active pixel sensor produced by means of CMOS technology has compared with a pixel sensor based on amorphous silicon may be exploited.

In some embodiments, the photodiode is embedded in an epitaxial silicon layer (epitaxial Si; called epi-Si for short). Epi-Si layers possess the same crystal orientation as the Si substrate on which they have been applied or grown.

The thickness of the epitaxial silicon layer may be embodied as a function of, or matched to, the wavelength of the scintillator layer in order to provide high quality imaging. In this connection the thickness of the epi-Si layer may be chosen such that a majority, for example between 90% and 98%, in particular 95%, of the light generated in the scintillator layer is absorbed and consequently contributes toward the imaging. On the other hand it may be advantageous not to choose an epi-Si layer of greater thickness in order to limit the generation of direct hits. The depth at which the BOX layer is introduced under the photodiode embedded in the epi-Si layer or into the epi-Si layer itself may limit the thickness of the epi-Si layer.

According to a further embodiment the buried oxide layer is between 40 nm and 100 nm thick. Such a thickness may provide adequate insulation against the conduction of electrical charges by direct hits and can be fabricated quickly and without great investment in resources.

Figure 1:
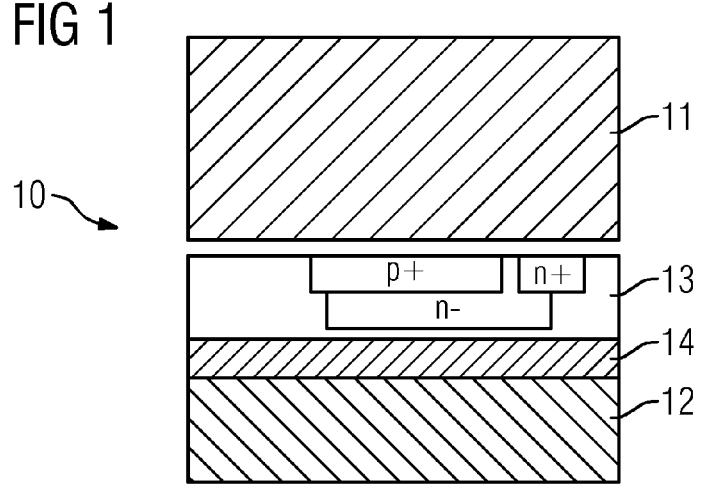
FIG. 1 shows a section through an example pixel element having a buried oxide layer, according to certain embodiments.

FIG. 1 shows an example pixel element which has a silicon layer 11, a CMOS photodiode 13, a silicon substrate 12 and a buried oxide (BOX) layer 14 sandwiched between the silicon substrate 12 and the photodiode 13, according to certain embodiments. The photodiode is mounted onto a silicon wafer as an integrated circuit by means of CMOS technology, epitaxial methods (e.g. chemical vapor deposition (CVD) and doping processes) being used for this purpose. CMOS technology and the manufacture of integrated components such as photodiodes and field effect transistors, for example, is a well-known technology. Epi-Si layers are grown onto the silicon substrate e.g. by means of CVD; the epi-Si layer possesses the same crystal orientation as the substrate. Doping (n+, p+, n−) is likewise introduced according to known methods such as e.g. ion implantation.

A buried oxide (BOX) layer may also be applied onto the silicon wafer by means of technology of said kind. BOX layers are $SiO_2$ layers below the surface of the substrate which are introduced into the silicon substrate for example by means of ion implantation of very high volumes of oxygen. Alternatively it is also possible first to produce the oxide layer during the manufacturing process and subsequently to apply the photodiode embedded in the epi-Si layer. The thickness of the epi-Si layer may correspond to the depth at which the BOX layer is incorporated below the surface of the photodiode.

The thickness of the epi-Si layer may be chosen to match the wavelength of the light generated by the scintillator layer during the absorption of X-ray radiation. Toward that end it may be chosen, e.g., in such a thickness that a majority, for example 90% to 98%, and in particular around 95%, of the generated light is absorbed. Since the wavelength of the light generated by the scintillator is dependent on its material composition, a precise match between the material of the scintillator and the thickness of the photodiode/epi-Si layer may be advantageous. The BOX layer itself may have a thickness of between 40 nm and 100 nm, for example, in order to provide good insulation against charges produced in the silicon substrate 12.

Figure 2:
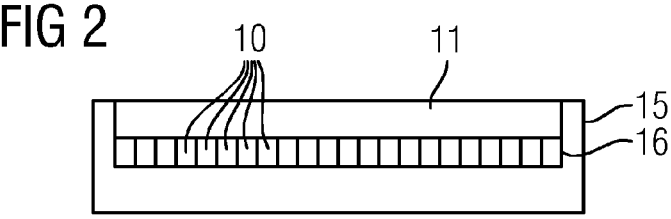
FIG. 2 shows a view of an example X-ray detector comprising a multiplicity of pixel elements, according to certain embodiments.

FIG. 2 shows an example X-ray detector 15 having an active array 16 comprising a multiplicity of pixel elements 10 as shown in FIG. 1. Sufficiently small pixel elements 10, for example in the order of magnitude of 150×150 μm or 100×100 μm or less, are used for this purpose. The scintillator layer 11 can also be embodied as a continuous layer arranged in the direction of the incident X-ray radiation over the entire active array 16. The impinging X-ray quanta are absorbed in the scintillator layer and converted into light. The light is then converted into a measurable electrical signal in the underlying photodiode and read out.

The use of CMOS technology for producing the integrated photodiode may provide fast, loss-free conversion and readout of the measurable electrical signals. With an X-ray detector of said type the X-ray quanta generate a measurable signal in the region of the same pixel element in which they are absorbed. Some X-ray quanta which are inadvertently absorbed in the silicon substrate and generate electrical charges there due to the semiconductor material cannot contribute to a noise signal on account of the insulating effect created by the BOX layer. The X-ray detector may therefore provide improved and more noise-free imaging, in particular also in the case of image series produced with a relatively low X-ray dose (known as fluoro scenes).

Figure 3:
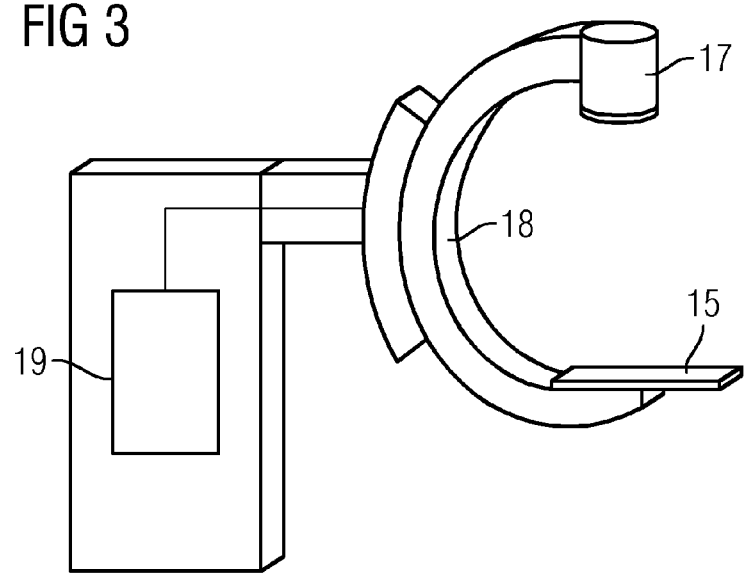
FIG. 3 shows an example X-ray device having an example X-ray detector according to certain embodiments.

FIG. 3 shows an example medical X-ray device that has an X-ray detector 15 according to certain embodiments. As shown, the X-ray detector 15 may be arranged together with an X-ray source 17 on a C-arm 18 which is adjustable with respect to an examination object. X-ray detector 15 and X-ray source 17 may be controlled by a system controller 19 for the purpose of recording X-ray images of the examination object.

Thus, certain embodiments provide an X-ray detector having an active array comprising pixel elements for the purpose of detecting X-ray radiation to enable high-quality X-ray imaging, wherein each pixel element has a scintillator layer for converting X-ray radiation into light and a photodiode produced by means of CMOS technology for converting light into a measurable electrical signal, and wherein the pixel elements are arranged on a silicon substrate and a BOX (buried oxide) layer is arranged between the silicon substrate and the photodiode.

What is claimed is:

1. An X-ray detector comprising:
   an active array of pixel elements for detecting X-ray radiation,
   wherein each pixel element has a scintillator layer for converting X-ray radiation into light and a photodiode produced by means of CMOS technology for converting light into a measurable electrical signal, and
   wherein the pixel elements are arranged on a silicon substrate and a buried oxide layer is sandwiched between the silicon substrate and the photodiode, the buried oxide layer being sized and configured to prevent X-ray-induced charges generated in the substrate from diffusing to the photodiode.

2. The X-ray detector of claim 1, wherein the photodiode is embedded in an epitaxial silicon layer.

3. The X-ray detector of claim 2, wherein the thickness of the epitaxial silicon layer corresponds to the wavelength of the light that can be generated in the scintillator layer.

4. The X-ray detector of claim 3, wherein the thickness of the epitaxial silicon layer is selected such that between 90% and 98% of the light generated by the scintillator layer can be absorbed.

5. The X-ray detector of claim 4, wherein the thickness of the epitaxial silicon layer is selected such that about 95% of the light generated by the scintillator layer can be absorbed.

6. The X-ray detector of claim 1, wherein the buried oxide layer has a thickness of between 40 nm and 100 nm.

7. The X-ray detector of claim 1, wherein the active array is embodied as an active pixel sensor.

8. A medical X-ray device, comprising:
   an X-ray source, and
   an X-ray detector comprising:
      an active array of pixel elements for detecting X-ray radiation,
      wherein each pixel element has a scintillator layer for converting X-ray radiation into light and a photodiode produced by means of CMOS technology for converting light into a measurable electrical signal, and
      wherein the pixel elements are arranged on a silicon substrate and a buried oxide layer is sandwiched between the silicon substrate and the photodiode, the buried oxide layer being sized and configured to prevent X-ray-induced charges generated in the substrate from diffusing to the photodiode.

9. The X-ray device of claim 8, wherein the photodiode is embedded in an epitaxial silicon layer.

10. The X-ray device of claim 9, wherein the thickness of the epitaxial silicon layer corresponds to the wavelength of the light that can be generated in the scintillator layer.

11. The X-ray device of claim 10, wherein the thickness of the epitaxial silicon layer is embodied in such a way that between 90% and 98% of the light generated by the scintillator layer can be absorbed.

12. The X-ray device of claim 11, wherein the thickness of the epitaxial silicon layer is selected such that about 95% of the light generated by the scintillator layer can be absorbed.

13. The X-ray device of claim 8, wherein the buried oxide layer has a thickness of between 40 nm and 100 nm.

14. The X-ray device of claim 8, wherein the active array is embodied as an active pixel sensor.

* * * * *